(12) United States Patent
Stievater et al.

(10) Patent No.: US 8,459,123 B2
(45) Date of Patent: Jun. 11, 2013

(54) MICROMECHANICAL CHEMICAL SENSORS WITH MULTIPLE CHEMOSELECTIVE RESONANT ELEMENTS AND FREQUENCY DIVISION MULTIPLEXED READOUT

(75) Inventors: Todd H. Stievater, Arlington, VA (US); William S Rabinovich, Silver Spring, MD (US); Nicolas A Papanicolaou, Potomac, MD (US); Robert Bass, Columbia, MD (US); Jennifer L Stepnowski, Alexandria, VA (US); R Andrew McGill, Lorton, VA (US)

(73) Assignee: The United States of America, as represented by the Secretary of the Navy, Washington, DC (US)

( * ) Notice: Subject to any disclaimer, the term of this patent is extended or adjusted under 35 U.S.C. 154(b) by 923 days.

(21) Appl. No.: 12/569,691

(22) Filed: Sep. 29, 2009

(65) Prior Publication Data

US 2010/0139406 A1    Jun. 10, 2010

Related U.S. Application Data

(63) Continuation-in-part of application No. 12/488,472, filed on Jun. 19, 2009, now abandoned.

(60) Provisional application No. 61/073,810, filed on Jun. 19, 2008.

(51) Int. Cl.
*G01B 9/02* (2006.01)

(52) U.S. Cl.
USPC ............................ 73/657; 204/400; 73/655

(58) Field of Classification Search
USPC ................ 73/655, 653, 654, 657; 422/82.01, 422/68.01, 98, 68.1; 204/400, 403.06, 403.1
See application file for complete search history.

(56) References Cited

U.S. PATENT DOCUMENTS

| | | | | |
|---|---|---|---|---|
| 2,993,876 A * | 7/1961 | McGlamery | ................... | 428/397 |
| 4,454,522 A * | 6/1984 | de Lozanne | ..................... | 257/36 |
| 5,135,852 A * | 8/1992 | Ebersole et al. | ................ | 435/39 |
| 5,306,644 A * | 4/1994 | Myerholtz et al. | ............ | 436/149 |
| 5,520,862 A * | 5/1996 | Face et al. | ..................... | 264/40.1 |
| 5,658,732 A * | 8/1997 | Ebersole et al. | ............. | 435/6.11 |
| 5,705,399 A * | 1/1998 | Larue | ............................ | 436/501 |
| 5,719,324 A * | 2/1998 | Thundat et al. | .............. | 73/24.01 |

(Continued)

OTHER PUBLICATIONS

Abedinov N., Popov C., Yordanov Z., Ivanov T., Gotszalk T., Grabiec P., Kulisch W., Rangelow I.W., Filenko D., Shirshov Y., "Chemical recognition based on micromachined silicon cantilever array," J. Vac. Sci. Technol. B., vol. 21, No. 6, pp. 2931-2936 (2003).

(Continued)

*Primary Examiner* — Peter Macchiarolo
*Assistant Examiner* — Samir M Shah
(74) *Attorney, Agent, or Firm* — Amy L. Ressing; Sally A. Ferrett

(57) ABSTRACT

Micro-opto-mechanical chemical sensors and methods for simultaneously detecting and discriminating between a variety of vapor-phase analytes. One embodiment of the sensor is a photonic microharp chemical sensor with an array of closely spaced microbridges, each differing slightly in length and coated with a different sorbent polymer. The microbridges can be excited photothermally, and the microbridges can be optically interrogated using microcavity interferometry. Other actuation methods include piezoelectric, piezoresistive, electrothermal, and magnetic. Other read-out techniques include using a lever arm and other interferometric techniques.

26 Claims, 12 Drawing Sheets

U.S. PATENT DOCUMENTS

| | | | | |
|---|---|---|---|---|
| 5,807,758 | A | * | 9/1998 | Lee et al. ............... 436/526 |
| 5,811,815 | A | * | 9/1998 | Marshall et al. ......... 250/370.06 |
| 5,945,280 | A | * | 8/1999 | Fawcett et al. .............. 435/6.11 |
| 6,157,404 | A | * | 12/2000 | Marshall et al. ........... 348/216.1 |
| 6,289,717 | B1 | * | 9/2001 | Thundat et al. ............... 73/23.2 |
| 6,710,355 | B2 | * | 3/2004 | Youngner ................ 250/458.1 |
| 7,062,110 | B2 | * | 6/2006 | Freeman et al. ............... 385/12 |
| 7,112,760 | B2 | * | 9/2006 | Ishikawa et al. ......... 219/121.76 |
| 7,344,678 | B2 | * | 3/2008 | Majumdar et al. ......... 422/82.01 |
| 7,673,517 | B2 | * | 3/2010 | Stievater et al. ............... 73/653 |
| 7,691,583 | B2 | * | 4/2010 | Craighead et al. ............. 435/7.1 |
| 7,924,423 | B2 | * | 4/2011 | Van Neste et al. ............ 356/432 |
| 7,961,313 | B2 | * | 6/2011 | Van Neste et al. ............ 356/311 |
| 8,080,796 | B1 | * | 12/2011 | Van Neste et al. ......... 250/338.1 |
| 8,194,246 | B2 | * | 6/2012 | Thundat et al. ............... 356/311 |
| 8,349,611 | B2 | * | 1/2013 | Loverich et al. ............... 436/86 |
| 2002/0102743 | A1 | * | 8/2002 | Majumdar et al. ............ 436/518 |
| 2002/0166962 | A1 | * | 11/2002 | Roukes et al. ................ 250/306 |
| 2006/0165342 | A1 | * | 7/2006 | Pau et al. ......................... 385/12 |
| 2007/0125150 | A1 | * | 6/2007 | Stievater et al. ............... 73/1.79 |
| 2008/0035846 | A1 | * | 2/2008 | Talghader et al. ......... 250/338.1 |
| 2008/0245135 | A1 | * | 10/2008 | Aubin et al. ................. 73/61.49 |

OTHER PUBLICATIONS

Adams, J.D., Parrott, G., Bauer, C., Sant, T., Manning, L., Jones, M. Rogers, B., "Nanowatt chemical vapor deposition with a self-cleansing, piezoelectric microcantilever array", Appl. Phys. Lett., vol. 83, No. 16, pp. 3428-3430, Oct. 2003.

Bubb, D. M., McGill, R. A., Horwitz, J. S., et al., "Laser-based processing of polymer nanocomposites for chemical sensing applications", Journal of Applied Physics, vol. 89, No. 10, pp. 5739-5739-46, May 2001.

Carr, D. W., Craighead, H. G., "Fabrication of nanoelectromechanical systems in single crystal silicon using silicon on insulator substrates and electron beam lithography", J. Vac. Sci. Technol. B, vol. 15, No. 6, pp. 2760-2763, Nov./Dec. 1997.

Cornila, C., Hierlemann, A., Lenggenhager, R., et al., "Capacitive sensors in CMOS technology with polymer coating", Sensors and Actuators B, vol. 24-25, pp. 357-361, 1995.

Fritz, J., M. K. Baller, H. P. Lang, H. Rothuizen, P. Vettiger, E. Meyer, H.J. Guntherodt, C. Gerber, and J. K. Gimzewski, "Translating Biomolecular Recognition into Nanomechanics", Science, vol. 288, p. 316-318, (Apr. 2000).

Gabrielson T.B., "Mechanical-thermal noise in micromachined acoustic and vibration sensors," IEEE Trans. Electron. Devices, vol. 40, pp. 903-909 (1993).

Gilbreath G. C., Rabinovich W. S., Meehan T. J., Vilcheck M. J., Stell M., Mahon R., Goetz P. G., Oh E., Vasquez J. A., Cochrell K., Lucke R. L., Mozersky S., "Progress in development of multiple-quantum-well retromodulators for free-space data links," Opt. Eng., vol. 42, pp. 1611-1617 (2003).

Goetz, P.G., Mahon, R., Stievater, T.H., Rabinovich,W.S., Binari S.C., "High-speed large-area surface-normal multiple quantum well modulators" SPIE vol. 5160, pp. 346-354, 2004, (conference date Aug. 4, 2003).

Hagleitner, C., Lange D., Hierlemann A., Brand O., Baltes H., "CMOS single-chip gas detection system comprising capacitive, calorimetric and mass-sensitive microsensors", IEEE J. Solid-State Circuits, vol. 37, p. 1867-1878, (Dec. 2002).

Hansen, K.M., Thundat, T., "Microcantilever biosensors", Methods: A Companion to Methods in Enzymology, vol. 37, No. 1, pp. 57-64, Sep. 2005.

Howe, R.T., Muller R. S., "Resonant-microbridge vapor sensor", IEEE Trans. Electron Devices vol. 33, p. 499-506, (1986).

Hu, Z., Seeley, T., Kosset, S., Thundat, T., "Calibration of optical cantilever deflection readers", Rev. Sci. Instrum., vol. 75, No. 2, pp. 400-404, Feb. 2004.

Lang H.P., Baller M.K., Berger R., Gerber C., Gimzewski J.K., Battiston F.M., Fornaro P., Ramseyer J.P., Meyer E., Guntherodt H.J., "An artificial nose based on a micromechanical cantilever array," Analytica Chimica Acta 393, 59-65 (1999).

Lavrik, N.V., Datskos, P.G. "Femtogram mass detection using photothermally actuated nanomechanical resonators", Applied Physics Letters, vol. 82, No. 16, pp. 2697-2699, Apr. 2003.

McGill R.A., Abraham M.H., Grate J.W., "Choosing polymer-coatings for chemical sensors," Chemtech vol. 24, No. 9, pp. 27-37 (1994).

Meyer, G., Amer, N.M., "Novel optical approach to atomic force microscopy", Appl. Phys. Lett., vol. 53, No. 12, Sep. 1988, pp. 1045-1047.

Ngoi, B.K.A., Venkatakrishnan, K., Tan, B., "Laser scanning heterodyne-interferometer for micro-components", Optical Communications, vol. 173, pp. 291-301, Jan. 2000.

Pinnaduwage, L. A., Boiadjiev V.,. Hawk J. E, and Thundat T., "Sensitive detection of plastic explosives witih self-assembled monolayer-coated microcantilevers", Appl. Phys. Lett., vol. 83, p. 1471-1473 (Aug. 2003).

Pruessner M.W., Stievater T.H., Rabinovich W.S., McGill R.A., Stepnowski J.L., "MEMS Chemical Sensors Using Waveguide Fabry-Perot Microcavities", Conference on Lasers and Electro-Optica, Optical Society of America, session CMJJ7, 2 pages, conference date May 2008.

Ricco A.J., Crooks R.M., Osbourn G.C., "Surface acoustic wave chemical sensor arrays: New chemically sensitive interfaces combined with novel cluster analysis to detect volatile organic compounds and mixtures," Acc. Chem. Res., vol. 31, pp. 289-296 (1998).

Rose-Pehrsson S.L., Grate J.W., Ballantine D.S., Jurs P.C., "Detection of hazardous vapors including mixtures using pattern-recognition analysis of responses from surface acoustic-wave devices," Anal. Chem., vol. 60, No. 24, pp. 2801-2811 (1988).

Savran C.A., Sparks A.W., Sihler, J., et al., "Fabrication and characterization of a micromechanical sensor for differential detection of nanoscale motions", J. Microelectromechanical Systems, vol. 11, No. 6, Dec. 2002, pp. 703-708.

Scholl, D., Everson, M.P., Jaklevic, R.C., "In situ force calibration of high force constant atomic force microscope cantilevers", Rev. Sci. Instrum., vol. 65, No. 7, pp. 2255-2257, Jul. 1994.

Senesac L.R., Dutta P., Datskos P.G., Sepaniak M.J., "Analyte species and concentration identification using differentially functionalized microcantilever arrays and artificial neural networks," Analytica Chimica Acta vol. 558, pp. 94-101 (2006).

Stievater, T.H., Rabinovich, W.S., Newman, H.S., Ebel, J.L., Mahon, R., McGee, D.J., Goetz, P.G., "Microcavity Interferometry for MEMS Device Characterization," Journal of Microelectromechanical Systems, vol. 12, Issue 1, p. 109-116(2003).

Stievater, T. H., Rabinovich, W. S., Ferraro, M. S., Papanicolaou, N. A., Boos, J. B., McGill, R. A., Stepnowski, J. L., Houser, E. J., "All-Optical Micromechanical Chemical Sensors," Applied Physics Letters, vol. 89, Issue 9, p. 091125-1-091125-3,(Sep. 2006).

Stievater T.H., Rabinovich W.S., Papanicolaou N.A., Bass R., and Boos J.B., "Measured limits of detection based on thermal-mechanical frequency noise in micromechanical sensors," Appl. Phys. Lett., vol. 90, No. 5, pp. 051114 (3 pages) (2007).

Stievater T.H., Rabinovich W.S., Newman, H.S., et al., "Measurement of thermal-mechanical noise in microelectromechanical systems", Appl. Phys. Lett., vol. 81, No. 10, p. 1779-1781, Sep. 2002.

Stievater, T. H., Rabinovich, W. S., Ferraro, M. S., Papanicolaou, N. A., Bass, R. Boos, J. B., Stepnowski, J. L., McGill, R. A., "Photonic microharp chemical sensors," Optics Express, vol. 16, No. 4, pp. 2423-2430, Feb. 6, 2008.

Thundat, T., Wachter, E. A., Sharp, S. L., Warmack, R., "Detection of mercury vapor using resonating microcantilevers", Appl. Phys. Lett. vol. 66, No. 13, pp. 1695-1697, Mar. 1995.

Thundat, T., Sharp, S.L., Fisher, W.G., Warmack, R.J., Wachter, E.A., "Micromechanical radiation dosimeter", Appl. Phys. Lett., vol. 66, No. 12, pp. 1563-1565, Mar. 1995.

Tortonese, M., Barrett, R.C., Quate, C.F., "Atomic resolution with an atomic force microscope using piezoresistive detection", Appl. Phys. Lett., vol. 62, No. 8, pp. 834-836, Feb. 1993.

Veijola T., "Compact models for squeezed-film dampers with inertial and rarefied gas effects," J. Micromech. Microeng., vol. 14, pp. 1109-1118 (2004).

Vignola, J.F., Liu, X., Morse, S.F., "Characterization of silicon micro-oscillators by scanning laser vibrometry", Rev. Sci. Instrum., vol. 73, No. 10, pp. 3584-3588, Oct. 2002.

Wachter, E.A., Thundat, T., Oden. P.I., Warmack, R.J., Datskos, P.G., Sharp, S.L., "Remote optical detection using microcantilevers", Rev. Sci. Instrum., vol. 67, No. 10, pp. 3434-3439, Oct. 1996.

Wachter, E.A., Thundat, T., "Micromechanical sensors for chemical and physical measurements", Rev. Sci. Instrum., vol. 66, No. 6, pp. 3662-3667, Jun. 1995.

* cited by examiner

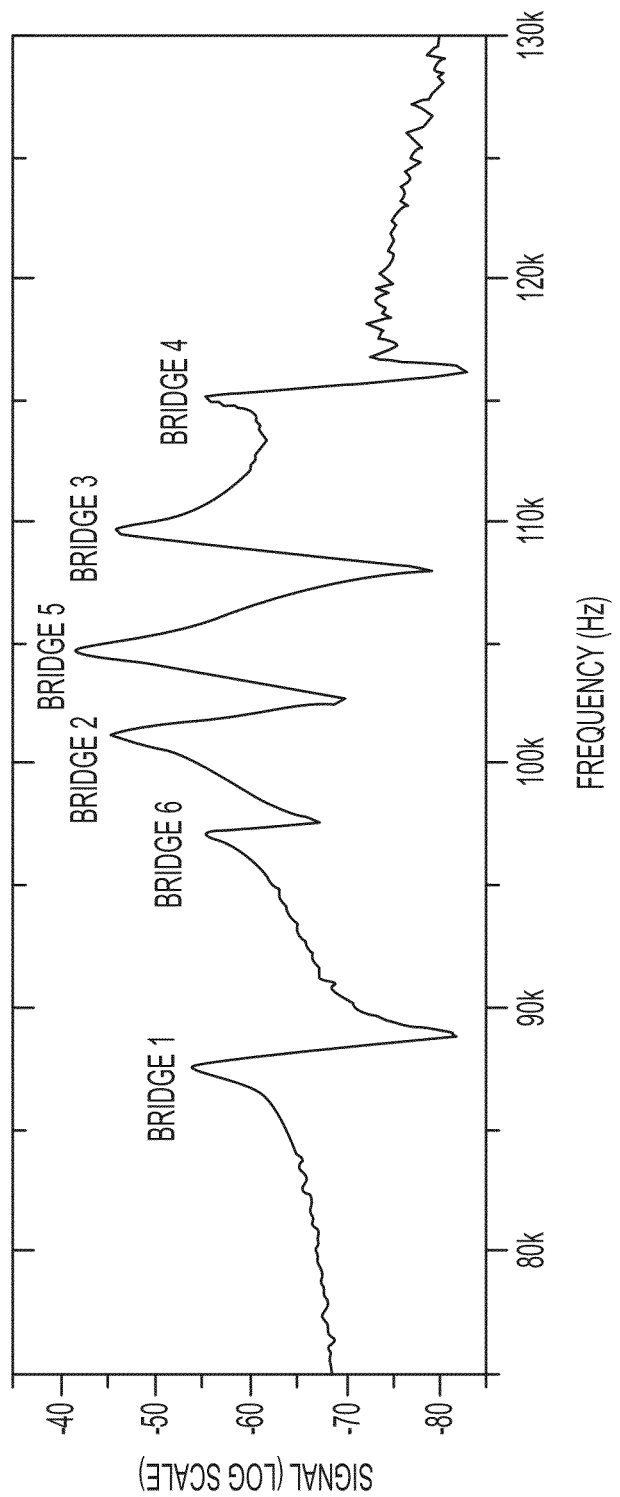

MICROMECHANICAL CHEMICAL SENSORS WITH MULTIPLE CHEMOSELECTIVE RESONANT ELEMENTS AND FREQUENCY DIVISION MULTIPLEXED READOUT

CROSS-REFERENCE TO RELATED APPLICATIONS

This Application is a continuation-in-part of U.S. patent application Ser. No. 12/488,472 filed on Jun. 19, 2009, which claims the benefit of U.S. Provisional Application 61/073,810 filed on Jun. 19, 2008, the entire disclosures of which are incorporated by reference herein.

BACKGROUND OF THE INVENTION

1. Technical Field

This application is related to micro-mechanical chemical sensors, and more particularly, to micro-mechanical sensors with chemoselective material layers operated in a dynamic mode.

2. Description of Related Technology

Small, portable, reusable chemical sensors that are both sensitive and selective are desired for applications ranging from remote sensing to counterterrorism to warfighter safety. One sensing technology that has been extensively studied to satisfy these criteria is arrays of sorbent polymer coatings as the sensing element of an "electronic nose", as described in R. A. McGill, M. H. Abraham, and J. W. Grate, "Choosing polymer-coatings for chemical sensors," Chemtech 24(9), 27-37 (1994); 2. A. J. Ricco, R. M. Crooks, and G. C. Osbourn, "Surface acoustic wave chemical sensor arrays: New chemically sensitive interfaces combined with novel cluster analysis to detect volatile organic compounds and mixtures," Acc. Chem. Res. 31, 289-296 (1998); and S. L. Rose-Pehrsson, J. W. Grate, D. S. Ballantine, and P. C. Jurs, "Detection of hazardous vapors including mixtures using pattern-recognition analysis of responses from surface acoustic-wave devices," Anal. Chem. 60(24), 2801-2811 (1988).

Micromechanical sensors can be classified into two general classes: (i) displacement-sensitive sensors that are operated in a static mode that is far below the device's mechanical resonant frequency; and (ii) resonant sensors that are operated in a dynamic mode at or near the device's mechanical resonance frequency.

Recent research has focused on arrays of ultra-sensitive microcantilevers whose sorption induced bending or resonant frequency change is read-out electronically or optically. See, for example, T. Thundat, E. A. Wachter, S. L. Sharp, and R. Warmack, "Detection of mercury-vapor using resonating microcantilevers," Appl. Phys. Lett. 66, 1695-1697 (1995) describing microcantilever sensors. N. Abedinov, C. Popov, Z. Yordanov, T. Ivanov, T. Gotszalk, P. Grabiec, W. Kulisch, I. W. Rangelow, D. Filenko, and Y. Shirshov, in "Chemical recognition based on micromachined silicon cantilever array," J. Vac. Sci. Technol. B. 21(6), 2931-2936 (2003), disclose electronic read-out of microcantilever sensors. L. R. Senesac, P. Dutta, P. G. Datskos, and M. J. Sepaniak, in "Analyte species and concentration identification using differentially functionalized microcantilever arrays and artificial neural networks," Analytica Chimica Acta 558, 94-101 (2006) disclose optical read-out of microcantilever sensors using time division multiplexing with optical measurement of cantilever deflection.

Recent work has included mass detection at the level of 6 femtograms, as described in N. V. Lavrik and P. G. Datskos, "Femtogram mass detection using photothermally actuated nanomechanical resonators," Appl. Phys. Lett. 82, 2697-2699 (2003). Chemical vapor detection at a level of 30 parts-per-trillion is described in L. A. Pinnaduwage, V. Boiadjiev, J. E. Hawk, and T. Thundat, "Sensitive detection of plastic explosives with self-assembled monolayer-coated microcantilevers," Appl. Phys. Lett. 83(7), 1471-1473 (2003).

Detection of single DNA base pairs has been demonstrated, as discussed in J. Fritz, M. K. Baller, H. P. Lang, H. Rothuizen, P. Vettiger, E. Meyer, H.-J. Guntherodt, C. Gerber, and J. K. Gimzewski, "Translating biomolecular recognition into nanomechanics," Science 288, 316-318 (2000).

Optical read-out approaches in particular have the potential for extremely high sensitivity, as discussed in T. H. Stievater, W. S. Rabinovich, H. S. Newman, R. Mahon, D. McGee, and P. G. Goetz, "Measurement of Thermal-Mechanical Noise in Microelectromechanical Systems," Appl. Phys. Lett. 81, 1779-1781 (2002). Remote optical interrogation of cantilever sensors is discussed in E. A. Wachter, T. Thundat, P. I. Oden, R. J. Warmack, P. G. Datskos, and S. L. Sharp, "Remote optical detection using microcantilevers," Rev. Sci. Instrum. 67(10), 3434-3439 (1996).

Optical read-out based on a beam deflection method is described in T. Thundat, E. A. Wachter, S. L. Sharp, and R. Warmack, "Detection of mercury-vapor using resonating microcantilevers," Appl. Phys. Lett. 66, 1695-1697 (1995) and L. R. Senesac, P. Dutta, P. G. Datskos, and M. J. Sepaniak, "Analyte species and concentration identification using differentially functionalized microcantilever arrays and artificial neural networks," Analytica Chimica Acta 558, 94-101 (2006). These systems can be difficult to miniaturize and/or package due to the physical separation required between the optical detector and the microcantilever sensor.

A system and method for optical interrogation of MEMs sensors using microcavity interferometry is disclosed in U.S. Patent Publication US2007-0125150A1 (Ser. No. 11/559, 119), to Todd H. Stievater, William S Rabinovich, Eric J Houser, Stanley Vincent Stepnowski, and R. Andrew McGill. The entire disclosure of this patent application is incorporated herein by reference. Optical interrogation of MEMS sensor is discussed in T. H. Stievater, W. S. Rabinovich, H. S. Newman, J. L. Ebel, R. Mahon, D. J. McGee, and P. G. Goetz, "Microcavity Interferometry for MEMS Device Characterization," J. Microelectromech. Syst. 12, 109-116 (2003). Photothermal actuation of a micromechanical system is disclosed T. H. Stievater, W. S. Rabinovich, M. S. Ferraro, N. A. Papanicolaou, J. B. Boos, R. A. McGill, and J. L. Stepnowski, "All-Optical Micromechanical Chemical Sensors," Appl. Phys. Lett. 89, 091, 125 (2006).

D. W. Can and H. G. Craighead, "Fabrication of nanoelectromechanical systems in single crystal silicon using silicon on insulator substrates and electron beam lithography," vol. 15, pp. 2760-2763 (AVS, 1997) discloses nano-scale resonators.

A photonic microharp chemical sensor is disclosed in T. H. Stievater, W. S. Rabinovich, M. S. Ferraro, N. A. Papanicolaou, R. Bass, J. B. Boos, J. L. Stepnowski, and R. A. McGill, "Photonic microharp chemical sensors," Opt. Express, Vol. 16, pp. 2423-2430 (February 2008), the entire disclosure of which is incorporated herein in its entirety.

BRIEF SUMMARY

An embodiment of the invention is directed to a chemical sensor comprising a substrate transparent at operational wavelengths, with a first reflective layer disposed on the substrate, a plurality of microbridges, and support posts arranged at each end of each end of the microbridges to connect the ends of the microbridge to the substrate. The microbridge, support posts, and substrate define a cavity between free portions of the microbridge and the substrate. Each of the microbridges includes reflective material. A chemoselective material is disposed on at least two of the microbridges. Each of the microbridges has a different fundamental resonance or mechanical flexural frequency. The microbridge and the reflective layer on the transparent substrate forming a Fabry-Perot etalon cavity. Each of the microbridges is adapted to receive laser light at a first frequency near its fundamental resonant frequency and to be photothermally actuated into resonance. Upon adsorption of a target chemical by the chemoselective material on one of the microbridges, a detected change in the resonant frequency of that microbridge indicates adsorption of the target chemical by the chemoselective layer on that microbridge.

A different chemoselective material can be disposed on each of the plurality of microbridges. At least one of the microbridges can be uncoated and free of chemoselective material.

Each of the microbridges can have a different length.

The system can also include a network analyzer for receiving reflected light from the sensor and determining the change in resonant frequencies of each of the microbridges.

In several examples, the plurality of microbridges includes four microbridges or includes six microbridges.

Another aspect of the invention is directed to a method for sensing presence of a target chemical using a micro-opto-mechanical chemical sensor having a transparent substrate, a reflective material disposed on the transparent substrate, and a plurality of reflective microbeams, each microbeam being connected at both ends to the substrate, each microbeam having a different fundamental resonant frequency, at least two of the microbeams having a different chemoselective material layer disposed thereon for detecting different target chemicals. The method includes receiving at the plurality of microbeams amplitude modulated laser energy at a first wavelength, with the microbeams being photothermally excited into resonance at the frequency of amplitude modulation, receiving at the reflective microbridge and at the reflective layer optical energy at a second wavelength, with the reflective microbeam and reflective layer reflecting the optical energy toward a receiver, and interferometrically determining a change in reflectivity of the microbeams, wherein a change in reflectivity of one of the microbeams indicates a change in resonant frequency of the microbeam and adsorption of the target chemical by that microbeam.

The frequency of amplitude modulation can be close to the fundamental resonant frequencies of the microbeams. Each of the microbeams can have a different length. A different chemoselective material is disposed on each of the microbridges. At least one of the microbridges can be uncoated and free of chemoselective material.

The method can also include receiving reflected light at a photodetector, transmitting signals from the photodetector to a network analyzer, and determining at said network analyzer the change in resonant frequencies of each of the microbridges.

The method can also include distinguishing which target chemical is present based on said change in resonant frequencies.

In examples, the sensor includes four or six microbridges.

Another aspect of the invention is directed to sensing a change in mass of a plurality of reflective microbeams in a sensor, the sensor having a reflective layer disposed on a substrate and being spaced apart from the reflective microbeams. The method includes the microbeams receiving amplitude modulated laser energy at a first wavelength from a first laser and being photothermally excited into resonance at their resonant frequencies, each of the resonant frequencies being close to the frequency of amplitude modulation, the reflective microbridges and the reflective layer receiving optical energy at a second different wavelength from a second laser, said reflective microbeams and reflective layer reflecting the optical energy toward a receiver, and interferometrically determining a change in reflectivities of the microbeam. A change in reflectivity indicates a change in resonant frequency of the microbeam and a change in mass of that microbeam, with the change in mass resulting from adsorption of a target chemical by a chemoselective material disposed on the microbeam.

The method can also include combining said amplitude modulated laser energy at a first wavelength from a first laser and said optical energy at a second and said optical energy at a second wavelength in a wave division multiplexer, and transmitting the combined energy to the sensor through a single optical fiber aperture.

Additional features will be apparent from the following drawings and detailed description of embodiments of the invention.

BRIEF DESCRIPTION OF THE DRAWINGS

FIG. 11 illustrates the response of a HC coated microbridge on a micro-opto-mechanical chemical sensor to DMMP at a concentration of about 17 parts per billion.

DETAILED DESCRIPTION OF EMBODIMENTS OF THE INVENTION

Figure 1A:
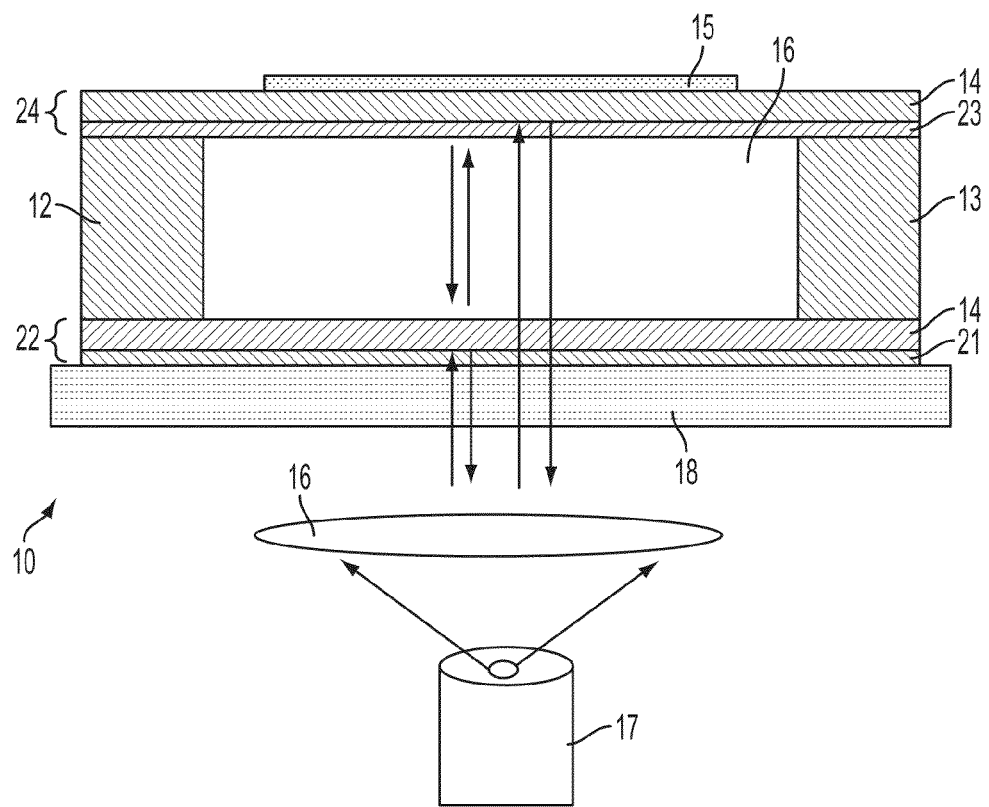
FIG. 1A is a side view of micro-opto-mechanical chemical sensor in accordance with an embodiment of the invention.
Figure 1B:
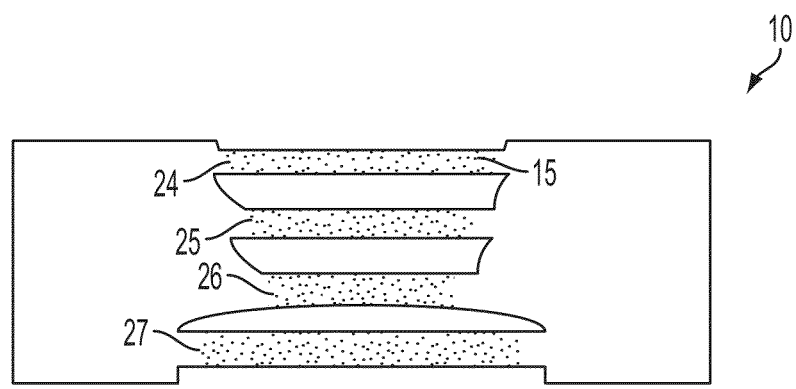
FIG. 1B is a top view of the sensor of FIG. 1A.
Figure 1C:
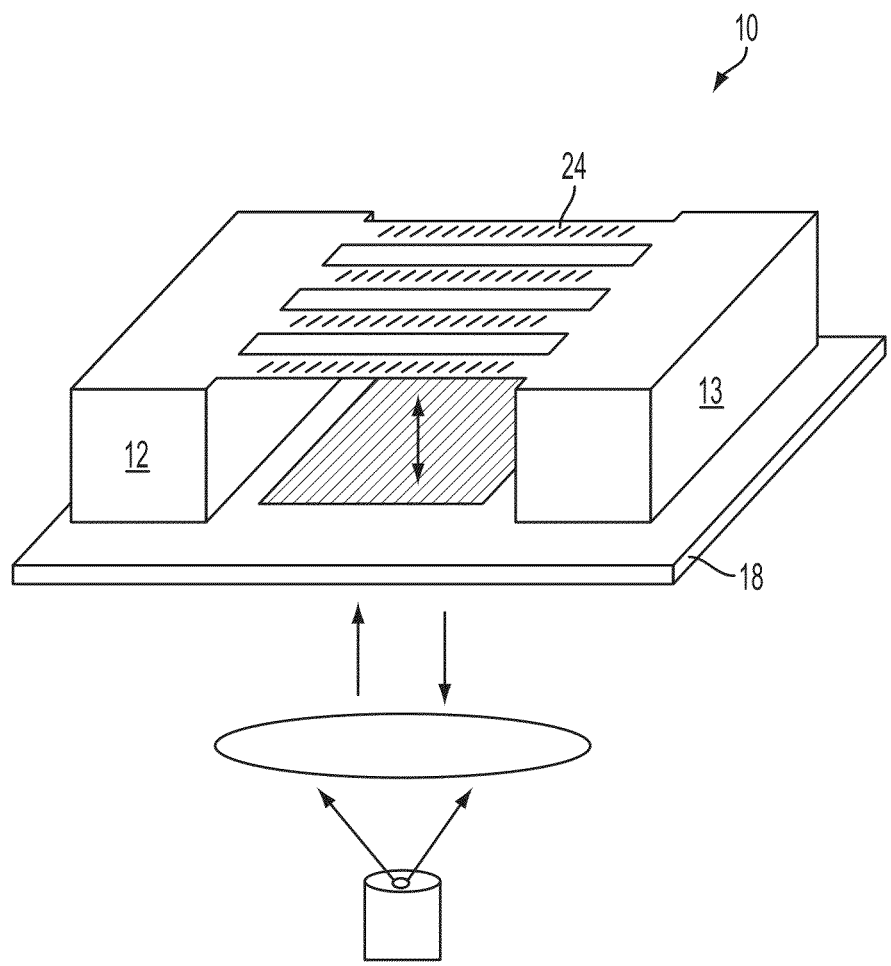
FIG. 1C is another view of the micro-opto-mechanical chemical sensor showing interrogation and actuation laser light incident on the sensor.

FIGS. 1A, 1B, and 1C illustrate a novel micro-opto-mechanical chemical sensor 10 in accordance with an embodiment of the invention.

The sensor 10 uses a photonic microharp design, and includes an array of closely spaced microbridges, each differing slightly in resonant frequency and each coated with a different chemoselective sorbent polymer. The chemoselective polymer layer on the microbridge allows the sensor to detect the presence of different target chemical compounds using an all-optical technique. The sensing procedure is based on detecting a shift in the resonant frequency of each of the microbridges that is induced by the absorption of chemical vapors by the chemoselective polymer.

In this example, the microbeams are configured as microbridges, with a support post at each end of the bridges, although microcantilevers or other resonant structures that can be excited into resonance can also be used as the resonant elements.

Because each micromechanical resonant structure (e.g., each microbridge) differs slightly in a particular mechanical property (e.g., length, width, intrinsic strain, material, etc.) the microstructures will have different inherent fundamental mechanical resonant frequency. The difference in resonant frequency is preferably at least a few percent between any two microstructures.

The microbridges are photothermally actuated, and optically interrogated using microcavity interferometry, as discussed in further paragraphs. Simultaneous measurements of the fundamental flexural resonant frequency of each microbridge allow the real-time detection and discrimination of a variety of vapor-phase analytes. The vapor-phase analytes include, but are not limited to, DMMP and hydrocarbons such as toluene, as discussed in later paragraphs.

FIG. 1A is a side view of the sensor system.

The substrate 18 is transparent at the operational wavelengths of the system to include a range including the wavelength of the optical interrogation signal and the returning signal wavelength. A suitable substrate is sapphire, glass, or a thin silicon.

The interrogation light is preferably positioned to be transmitted through the transparent substrate 18. A portion of the light is reflected by the reflective layer 22 disposed in or on the transparent substrate 18. The remaining portion of the light is transmitted through the cavity 16 to the microbridge 24. The microbridge 24 is or includes a reflective material such as gold, and the interrogation light is reflected by microbridge 24.

The microbridge 24 and the reflective layer of the substrate form an optical Fabry-Perot etalon cavity.

In an exemplary embodiment, several or all of the microbridges have a chemoselective material 15 deposited on the surface of the microbridge opposite the surface of the microbridge facing the substrate. The chemoselective material can be a chemoselective polymer layer. As the chemoselective material 15 sorbs its target chemical, the mass, and therefore, the resonant frequency of the microbridge 24 changes. The change in resonant frequency of the microbridge is detected interferometrically, as discussed in further detail in later paragraphs.

As shown in FIG. 1B, each of the microbridges 24, 25, 26, and 27 has a different length, and therefore, a different inherent fundamental mechanical resonant frequency. Each of the microbridges is coated with a different chemoselective sorbent polymer, so each microbridge adsorbs a different target chemical class.

Two lasers, operating at two different wavelengths, are used to excite and interrogate the microcavity. In an exemplary embodiment, an optical fiber 17 and optical lens 16 illuminate the sensor.

Figure 2A:
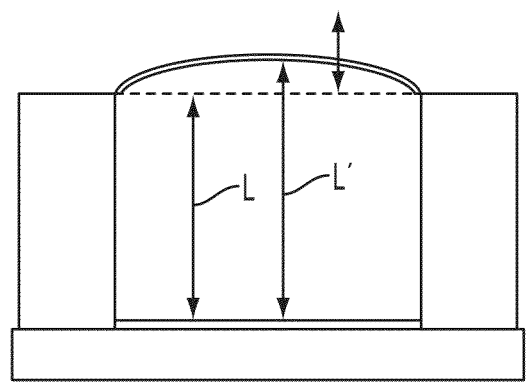
FIGS. 2A and 2B illustrate the motion of a microbridge of the sensor when photothermally actuated.
Figure 2B:
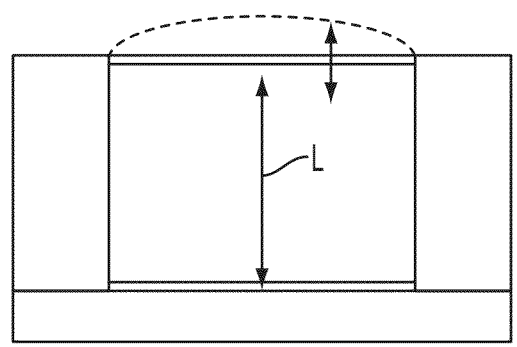

A first laser (the "activation" or "excitation" laser) is an amplitude modulated laser, or a CW laser with a modulator, which photothermally excites the microbridges. When the amplitude of the activation laser energy increases, the amplitude laser energy heats the microbridges, causing them to expand and to move out of their original positions, as shown in FIG. 2A. This deflection changes the cavity length L between the top reflective layer and the bottom reflective layer. As the amplitude of the activation laser energy decreases, the microbridges cool, causing them to contract and move back into their original positions, as shown in FIG. 2B. The frequency of the amplitude modulation (the frequency at which the laser energy is modulated) is matched to be near the fundamental flexural frequencies of the microbeams, so the modulation photothermally excites each of the microbeams to resonate at its individual inherent fundamental frequency.

Referring again to FIG. 1A, the cavity 16 between each microbridge and the bottom reflector is interrogated by the second laser (the "interrogation" or "read-out" laser), or other optical interrogation source. Suitable optical lenses 16 or other optical devices change the optical spot diameter, if necessary, to ensure that the interrogation optical energy reaches all of the microbridges in the sensor. A single optical spot is thus focused on the sensor.

Figure 3:
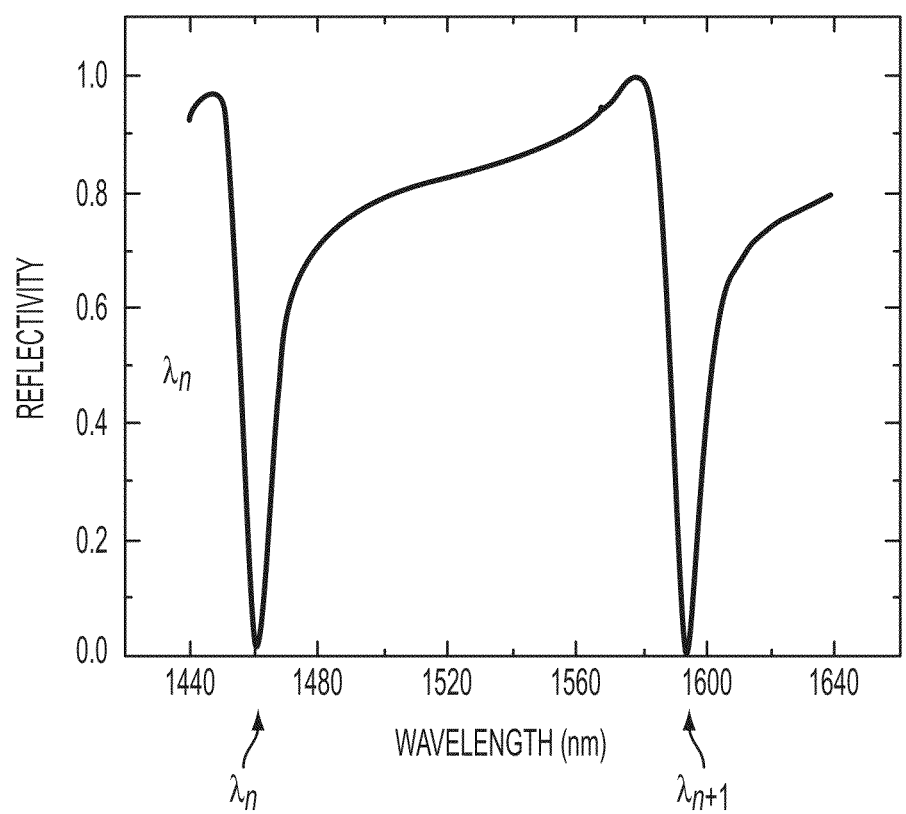
FIG. 3 illustrates the optical reflectivity spectrum of a microharp sensor, showing two Fabry-Perot etalon modes.

Each of the reflective microbridges, together with the bottom reflector 22 form a microcavity that exhibit etalon modes that are characterized by regularly spaced minima in the reflection spectrum. These modes arise from the interference of light reflected off the ends of the cavity. Parallel reflectors form a Fabry-Perot etalon. The wavelengths of these etalon modes depend on the length of the microcavity, and in a Fabry-Perot etalon, the wavelength of an etalon mode is $\lambda_n=2L/(n+1)$, where $\lambda_n$ is the wavelength of the nth mode, with n=0, 1, 2, . . . and L is the cavity length. FIG. 3 illustrates microcavity interferometry modes $\lambda_n$ and $\lambda_{n+1}$ in an etalon cavity formed by a gold microbridge and a sapphire substrate with a thin gold layer on the substrate. Movement of the microbridge changes the cavity length, which in turn changes the reflectivity from the cavity and shifts the wavelength of the etalon mode.

The second laser (the "readout" or "interrogation" laser) optically interrogates the microcavity formed by the top reflective layer and the bottom reflective layer, and operates at a wavelength different than that of the amplitude modulated laser excitation laser. The change in the cavity length results in a change in the amount of light reflected from the cavity. The readout laser wavelength should not coincide with the reflectance minima of an etalon mode for any of the microbridges, and preferably the wavelength will be at a point on the reflectance v. wavelength curve where the slope of the reflectance versus wavelength curve is large for each microbridge. For example, in FIG. 3, the readout laser wavelength is about midway between the reflection maxima and the reflection minima. The readout laser is preferably a tunable laser that can be adjusted to or set at the desired wavelength.

In an example embodiment, the frequency of amplitude modulation is swept over a frequency range that includes the flexural frequencies of the microbeams with and without sorbed chemicals in the chemoselective polymer layer. An optically detected change in the resonant frequency of any of the microbeams indicates a change in the mass of that microbeam that corresponds to sorption of that microbeam's target chemical.

The microbridges are fabricated on a transparent substrate 18 such as sapphire, glass, or a thin silicon wafer. The fabrication begins with an unpatterned deposition of a base layer 21 that bonds a gold layer 14 to the substrate 18. The base layer 21 can be about 3 nanometers of titanium, chrome, or nickel. The gold layer 14 is approximately 5 nanometers in thickness. The base layer 21 and the gold layer 14 form a bottom reflector 22. The bottom reflector 22 can be deposited by e-beam evaporation and is about 80% reflective at the 980 nm and 1550 nm wavelengths. Photolithography, electroplating, and lift-off techniques are used to form gold posts 12 and 13 and a sacrificial layer of material such as polymethylglutarimide (PMGI) in the region between the posts.

A second photolithographic and lift-off step, which defines the microbridges themselves, is used with a second electroplating or e-beam deposition of a base layer 23 followed by 1 micron of gold beam metal 14. The sacrificial PMGI material is etched with acetone to release the microbridge and form the cavity between the microbridge and the substrate, after which the sample is dried in a critical point dryer. The posts 12 and 13 support the microbridge 24.

The chemoselective polymers are then deposited onto the microbridges using a micropainting technique. Each polymer is first dissolved in an appropriate solvent. A microneedle is dipped into the solution and touched at least once onto the top of the microbridge, leaving a film with a thickness determined by the polymer concentration and the number of touches.

In this example, three polymers are deposited onto three different microbridges, and one microbridge is left uncoated. The first polymer is HCSA2 (HC), a hyperbranched carbosilane polymer developed at the Naval Research Laboratory that is functionalized with hydrogen bond acidic hexaflouroisopropanol groups, which targets hydrogen-phosphonate ester or nitroaromatic species such as dimethyl methylphosphonate (DMMP). The second polymer is polyethyleneimine (PEI), a commercial polymer that is strongly hydrophilic. The third polymer is CS3Ph2 (CS), a linear carbosilane developed at NRL that has phenyl functional groups and is used for detection of hydrocarbons.

As described below, dimethyl methylphosphonate, or methylphosphonic acid dimethyl ester (DMMP), can be detected at concentrations as low as 17 parts per billion using the micro-opto-mechanical sensors described herein. DMMP is a Chemical Weapons Convention schedule 2 chemical used in the synthesis of Sarin nerve gas, and can also be used as standalone as a simulant for Sarin training exercises and for calibration of detectors. Additional information about HCSA2 other chemoselective polymers is disclosed in E. J. Houser, D. L. Simonson, J. L. Stepnowski, R. A. McGill, "Linear and hyperbranched hydrogen bond acidic poly(silylene-methylene)s for chemical sensor applications", Polymer Materials: Science & Engineering Science Vol. 88, pg. 548(2003), in R. A. McGill, M. H. Abraham, J. W. Grate, "Choosing polymer coatings for chemical sensors," CHEMTECH 24, pp. 27-37, 1994, and in U.S. Pat. No. 6,660,230 to R. A. McGill, and E. J. Houser, entitled "Linear chemoselective carbosilane polymers and methods for use in analytical and purification applications", the disclosures of which are incorporated by reference in their entireties.

Figure 4:
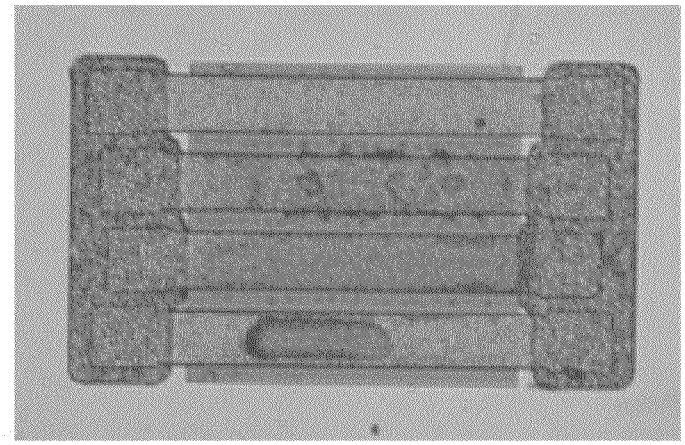
FIG. 4 is a photograph of a microharp with microbridges that form a portion of an exemplary microharp sensor.
Figure 5:
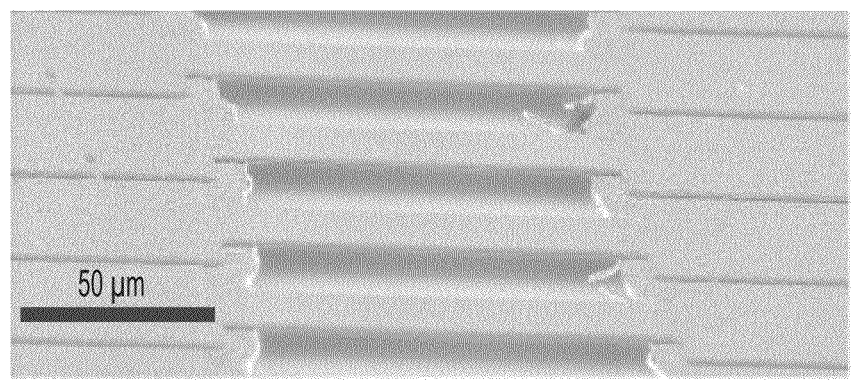
FIG. 5 is a scanning electron micrograph image of a gold microharp that forms a part of the micro-opto-mechanical chemical sensor prior to polymer deposition.

The micropainting technique has a spatial resolution of about 10 microns, an important feature for selectively coating a single microbridge in the microharp without contaminating the adjacent microbridges. A microharp with microbridges coated in this manner is shown in the photograph of FIG. 4. A scanning electron micrograph image of a gold microharp with four microbridges prior to polymer deposition is shown in FIG. 5.

Coating uniformities do not affect the optical properties of the microharp sensor, because the polymer coated surfaces of the microbridges are on the opposite face of the reflective microbridge, facing away from the bottom reflector and the interrogation and readout laser, thus, are not part of the Fabry-Perot microcavity.

Each individual microbridge in the sensor is an individual micromechanical resonator, and is interrogated simultaneously in a frequency-multiplexed manner. More specifically, each microbridge is slightly different, by a few percent, in a particular mechanical property, so the inherent resonant frequency of each microbridge is slightly different.

Figure 6:
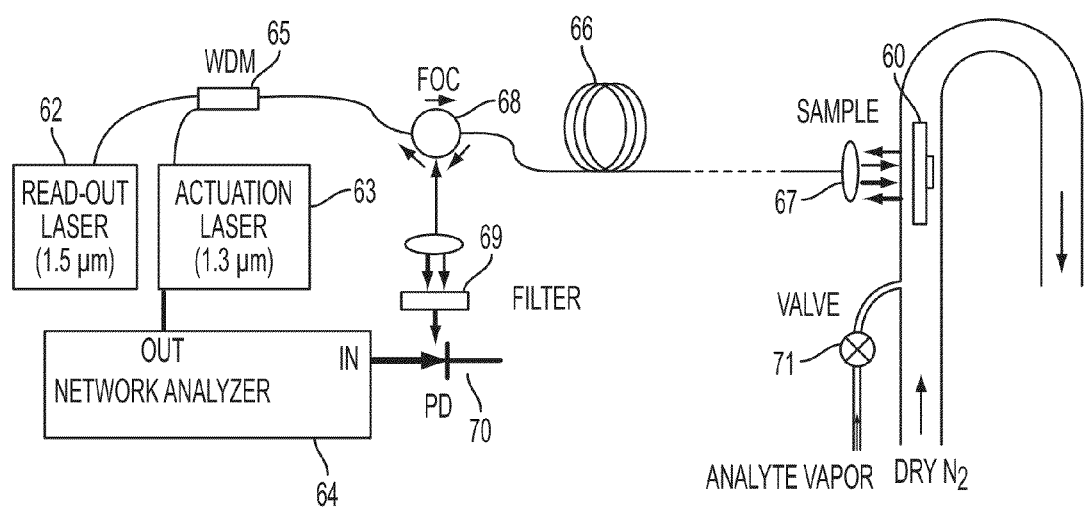
FIG. 6 illustrates a micro-opto-mechanical chemical sensor in operation in an experimental set up.

FIG. 6 illustrates the sensor in operation in an experimental set-up. The sensor is placed in a flow of dry N2, and the analyte vapor is introduced into the flow stream.

The readout laser 62 is a tunable laser diode with a wavelength between 1440 nm and 1640 nm. The readout laser measures the vertical displacement of the microbridge using microcavity interferometry. By tuning the wavelength of the readout laser to the side of a Fabry-Perot mode, changes in the distance between a microbridge and the substrate (cavity length, L) while the microbridge is photothermally excited are mapped into changes in the optical reflectivity. The photothermal actuation laser 63 resonantly drives the microbridges, allowing for high signal to noise determination of the resonant frequencies $f_0$. This, in turn, enables the measurement of small adsorption induced resonant frequency changes, $\Delta f$. The actuation laser 63 is amplitude modulated by a network analyzer 64, photothermally driving the microbridges into resonance.

In an exemplary embodiment, the actuation laser 63 produces an optical beam with a 1310 nanometer wavelength, and the readout laser 62 produces an optical beam with a tunable wavelength between 1440 and 1640 nm.

Light from the read-out laser and the actuation laser are combined in a single mode optical fiber by a fiber optic circulator 68, and transmitted through to the sensor location. Light exits the optical fiber, is transmitted through optional optics 67, and is incident on the substrate side of the sensor 60.

The read-out laser light is reflected by the bottom reflector on the substrate and by the reflective microbridges, is focused by the optics 67 into the single mode fiber. The circulator 68 sends the reflected read-out light from the microharp sensor 60 to an amplified photodetector 70 and the network analyzer 64. The filter arranged in the optical link between the circulator 68 and the photodetector filters any wavelengths outside the expected reflected read-out laser light range, so only the reflected read-out laser light reaches the photodetector. The network analyzer measures the reflected read-out laser light and accomplishes the frequency domain analysis for all the microbridges. The display screen of the network analyzer shows the results of the frequency domain analysis.

Figure 7:
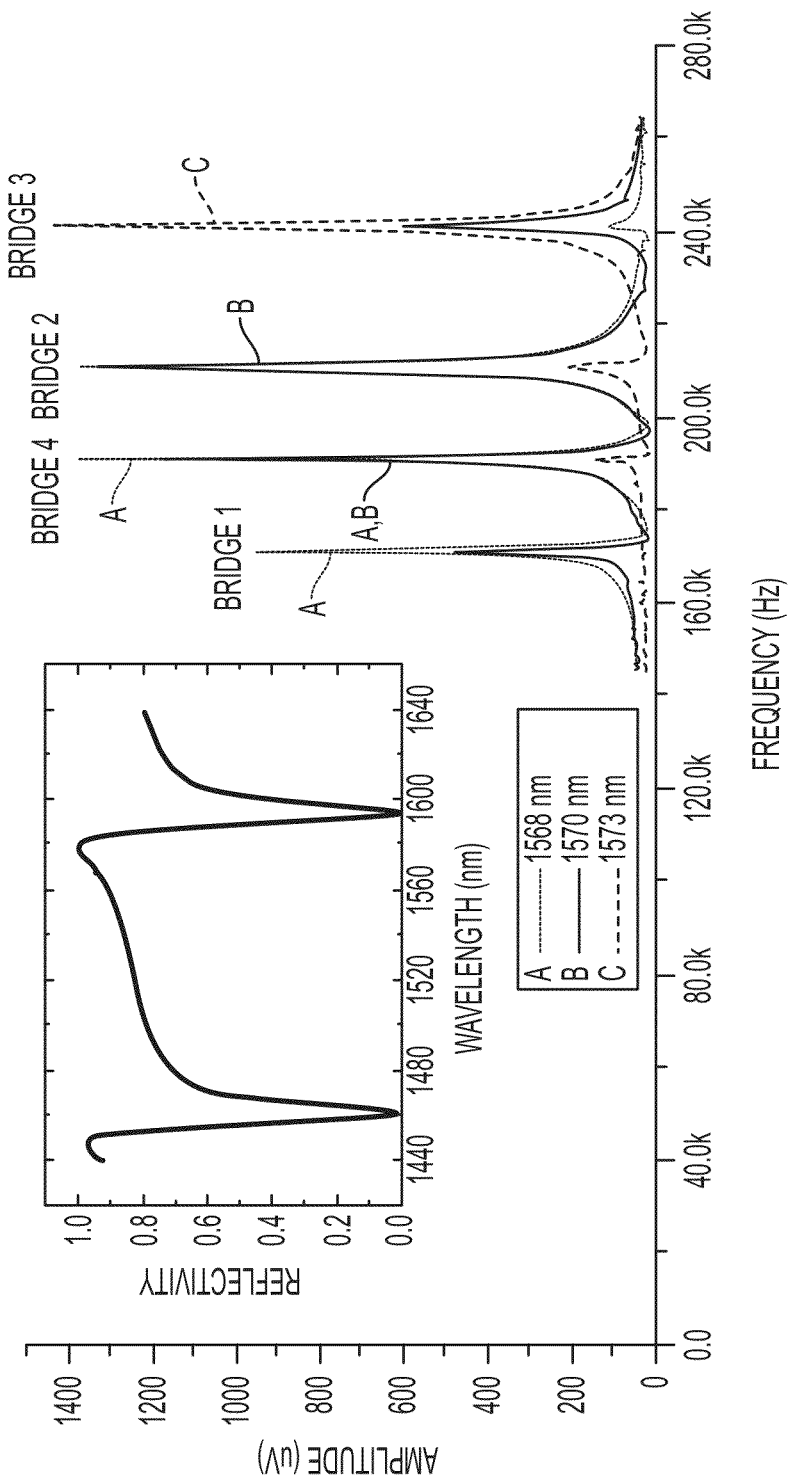
FIG. 7A illustrates the mechanical resonance spectrum of the microharp as demonstrated in the set-up of FIG. 6.

A mechanical vibration spectrum for a microharp sensor measured and analyzed in this manner is shown in FIG. 7. The mechanical resonance spectrum is obtained by the network analyzer for read-out laser light reflected by the microharp. Each resonance corresponds to the fundamental flexural mode of one microbridge in the microharp.

The x-axis of the FIG. 7 plot corresponds to the frequency at which the photothermal actuation laser is modulated and the y-axis is the signal at that frequency detected by the network analyzer and photodetector. The four clear peaks in the curve indicate the fundamental flexural resonance of each of the four microbridges on the microharp. The spacing of the resonances is a function of the specific length of each individual microbridge. Since each microbridge differs in length, slight bowing of the microbridges implies that the microcavity length, and thus the Fabry-Perot mode wavelength, also differs between microbridges, typically by a few nanometers. This causes the wavelength for optimal readout of microbridge displacement to vary by a few nanometers within the microharp, as indicated by the different spectra in FIG. 7.

In an example embodiment, the detection of chemical vapors is carried out by continuously monitoring the central resonant frequency of each microbridge within the microbridge while it is exposed to various concentrations of analytes. One of the microbridges (bridge 1 in FIG. 7) is left uncoated to serve as a reference to compensate for frequency drift due to temperature or pressure changes. To facilitate comparison between the microbridges, the change in resonant frequency of an $i^{th}$ microbridge ($\Delta f^i$) is normalized in the network analyzer by its resonant frequency at t=0 ($\Delta f_0^i$). Thus, the time dependent microharp can then be characterized by three parameters: $\Delta f^{(2)}/f_0^{(2)} - \Delta f^{(1)}/f_0^{(1)}$, the "HC" response in FIGS. 8A, 8B, and 8C, labeled as B2-B1 (81, 84, and 87); $\Delta f^{(3)}/f_0^{(3)} - \Delta f^{(1)}/f_0^{(1)}$, the "PEI" response in FIGS. 8A, 8B, and 8C, labeled as B3-B1 (82, 85, and 88); and $\Delta f^{(4)}/f_0^{(4)} - \Delta f^{(1)}/f_0^{(1)}$, the "CS" response in FIGS. 8A, 8B, and 8C, labeled as B4-B1 (83, 86, and 89).

Figures 8A, 8B, 8C:
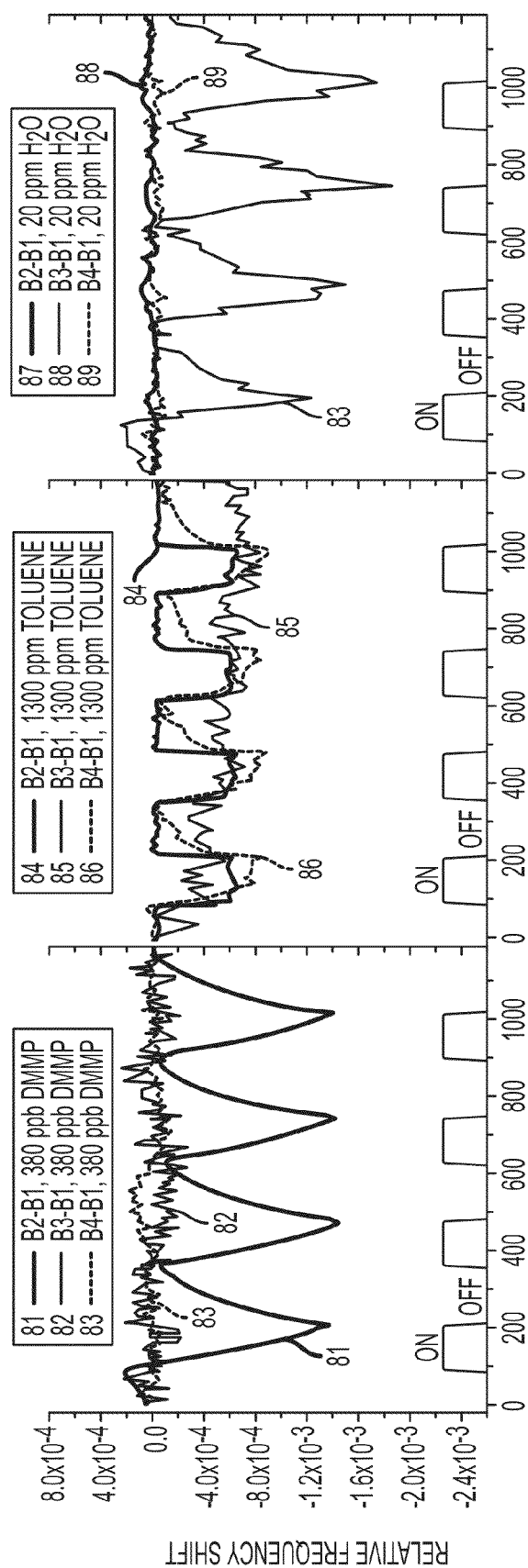
FIGS. 8A, 8B, and 8C illustrate responses of an exemplary micro-opto-mechanical chemical sensor to DMMP, toluene, and water vapor, respectively.

These three parameters are plotted in FIGS. 8A, 8B, and 8C for time varying exposure to DMMP (FIG. 8A), toluene (FIG. 8B), and water vapor (FIG. 8C). FIGS. 8A, 8B, and 8C show the response of the system to turning the valve that introduces the analyte into the system on and off. The data show a unique response for each analyte. Upon exposure to DMMP vapor in the parts per billion (ppb) range, only the microbridge coated with HC shows a response (FIG. 8A). Upon exposed to water vapor in the low parts per million (ppm) range, only the microbridge coated with PEI shows a response (FIG. 8C). Upon expose to toluene in the high ppm range, both the HC-coated microbridge and the CS-coated microbridge show a response, due to the comparable partition coefficients for these polymers for toluene adsorption. Nevertheless, the use of multiple coatings enables the clear discrimination between DMMP adsorption and toluene adsorption, even though the toluene concentration is three thousand times larger in these exposures.

Upon exposure to an analyte vapor, it takes a finite amount of time for the microbridge to reach a new equilibrium resonant frequency. These response times are limited by the polymer thickness and the diffusion rate of the particular analyte into the polymer. The exposure time of 120 seconds is approximately equal to the response time of toluene into CS and significantly longer than the response time of toluene into HC. However, this exposure time is clearly shorter than the full response time of DMMP into HC and water vapor into PEI.

Figure 9:
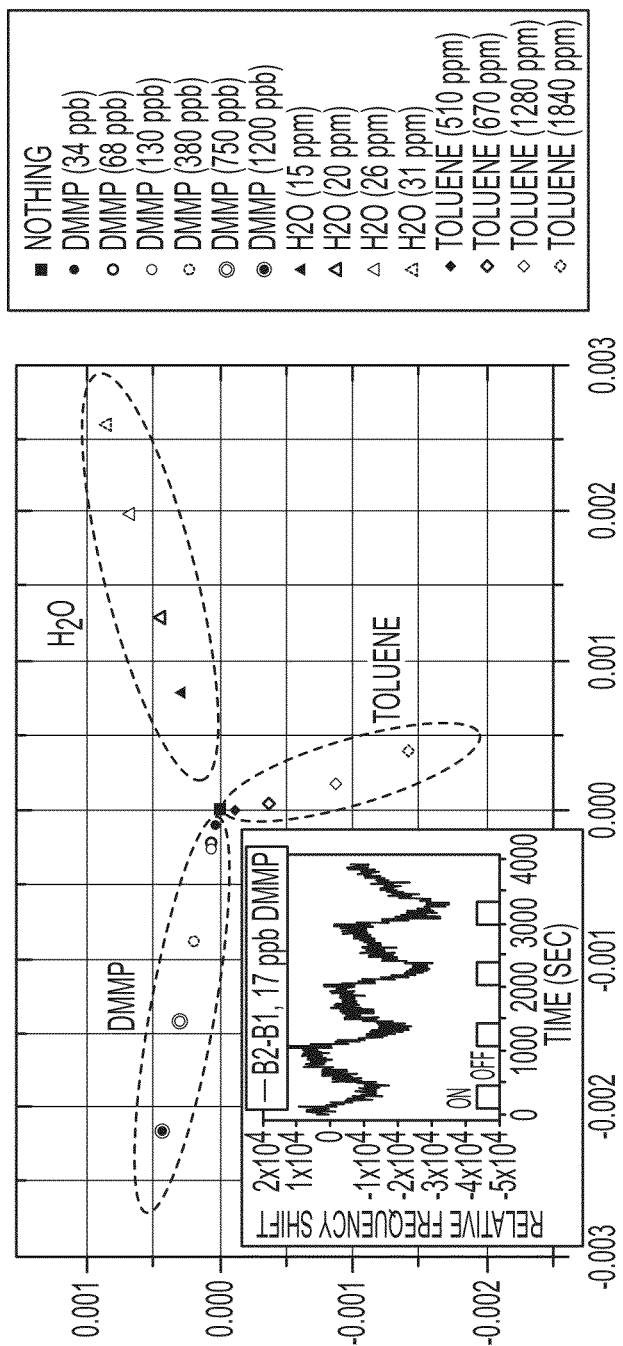
FIG. 9A is an analyte scatter plot using two-dimensional principal component analysis.

Two dimensional principal component analysis of the response of each analyte over a range of concentrations shows the ability of the microharp sensor to distinguish between these analytes. For each concentration of analyte, the relative differential frequency shift was found for each polymer after a 120 second exposure (e.g. for B2-B1, B3-B1, and B4-B1). This three dimensional vector was then transformed such that the two principal components of the transformed parameter space are the x-axis and the y-axis. Each analyte is represented by the angle of a vector, with the concentration represented by the vector amplitude. As shown in FIG. 9, the data show clear distinction between the three analytes tested, even at DMMP concentrations as low as 34 ppb.

Figure 10:
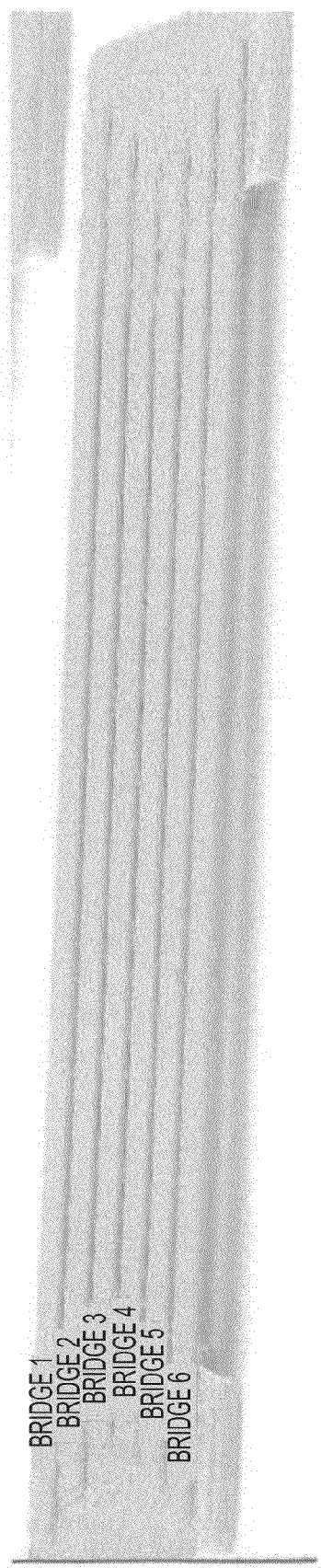
FIG. 10 is a scanning electron micrograph image of a gold microharp with six microbridges that forms a part of the micro-opto-mechanical chemical sensor in accordance with an embodiment of the invention.

Although the example discussed herein has a four-microbridge sensor, embodiments of the invention can also include larger numbers of microbridges in the array, allowing an even greater degree of sensing specificity. FIG. 10 is a scanning electron micrograph of a six-bridge microharp sensor ("sextuplet") that has been interrogated using two lasers in the same manner shown in FIG. 6 and described above. The sextuplet microharp can be coated with five different chemoselective coatings. The read-technique is the same as described above. FIG. 11 shows the mechanical response of the sextuplet obtained using all optical interrogation technique.

The network analyzer can input the results of the analysis into a computer that includes programmed instructions for recognizing the network analysis responses in the different resonant frequency bands for each target chemical/chemoselective material pair, and to output an indication of which target chemical/analyte is present in the environment. The computer can be desktop computer, a laptop computer, a mobile computer, a handheld computer or personal digital assistant, server computer, for example. The computer processing may also be practiced in distributed computing environments where tasks are performed by remote processing devices that are linked through a communications network. In one example, the computer includes at least one central processing unit ("CPU"), a system memory, including a random access memory ("RAM") and a read-only memory ("ROM"), and a system bus that couples the memory to the CPU. The computer can also includes a mass storage device for storing an operating system, application programs, and other program modules. The mass storage device and its associated computer-readable media provide non-volatile storage for the computer. Computer storage media includes volatile and non-volatile, removable and non-removable media implemented in any method or technology for storage of information such as computer-readable instructions, data structures, program modules or other data. Computer storage media includes, but is not limited to, RAM, ROM, EPROM, EEPROM, flash memory or other solid state memory technology, CD-ROM, digital versatile disks ("DVD"), or other optical storage, magnetic cassettes, magnetic tape, and magnetic disk storage or other magnetic storage devices.

While the examples shown above describe microbeams being photothermally actuated into resonance, the microbeams can be actuated into resonance by various other techniques. For example, the microbeams can be electrostatically actuated, actuated with voltage applied to a piezoelectric transducer either within or external to the microbeam for displacing the microbeam, or piezoresistively actuated. Other actuation techniques include electrothermal actuation and magnetic actuation, for example, by applying an electromagnetic field to an iron or manganese doped semiconductor component of the microbeam.

The changes in resonance frequencies can also be measured by other than the multiplexed interferometric optical readout system described above. For example, the deflections and frequencies of the microbeams can be measured using an optical lever arm technique or other interferometric techniques.

The system described herein has several advantages over other chemical sensor systems. The use of several microbridges operating at different frequencies and interrogation with a single readout laser allows the sensor to detect many different target chemical classes, without an equivalent increase in the number of read-out mechanisms (lasers, electrical probes, etc.). Allowing many sensor elements in an array to be used with a single readout signal eliminates device fabrication complexities that could result from having many readout signals, such as increased sensor size, increased power consumption, and possible cross-talk between readout elements.

In addition, the larger number of microbridge sensor elements in the sensor array can increase the specificity of the sensor's ability to discriminate the target analyte from other background analytes and effects. In contrast, single functionalized micromechanical elements intended to detect analytes at low levels can be susceptible to environmental and/or chemical interferences.

Note that the example described herein relies on different microbridge lengths to produce the difference in fundamental resonant frequencies of the microbridges. In other embodiments, the width, thickness, intrinsic strain, or material type, can be varied to produce different microbridge resonant frequencies. In addition, while the examples shown here illustrate microbridges with support on both ends, it is also suitable to implement the sensor using other types of microbeams capable of being driven into resonance, e.g., cantilevers, etc.

Obviously, many modifications and variations of the present invention are possible in light of the above teachings. It is therefore to be understood that the claimed invention may be practiced otherwise than as specifically described.

What is claimed as new and desired to be protected by Letters Patent of the United States is:

1. A sensor system comprising:
    a sensor for detecting the presence of a target vapor-phase analyte including:
        a substrate,
        a plurality of microbeams, each of the microbeams having a different fundamental resonant frequency, and at least two of the microbeams having a different sorbent material disposed thereon,
        each of the microbeams being connected to the substrate by at least one support,
        each of said microbeams adapted to be actuated into resonance; and
    an optical interrogation system including:
        an interrogation laser operating at a first wavelength configured to simultaneously interrogate the microbeams by illuminating all of the microbeams with a single laser spot, and
        a photodetector configured to receive reflected optical energy from the microbeams and to produce frequency division multiplexed electrical signals indicating the respective resonant frequency of each of the microbeams,
        wherein upon adsorption of the target analyte by the sorbent material on one of the microbeams, a detected change in the respective resonant frequency of said one of the microbeams indicates sorption of the target analyte by the sorbent material disposed on said one of the microbeams.

2. The sensor system according to claim 1, further comprising:
    at least one reference microbeam free of the sorbent material.

3. The sensor system according to claim 1, the sensor further including:
    a first reflective layer disposed on the substrate,
    each of the microbeams including reflective material,
    the substrate being transparent at operational wavelengths, and
    each of the microbeams and the substrate defining a Fabry-Perot etalon cavity between a free portion of each microbeam and the substrate.

4. The sensor system according to claim 3, in combination with:
    an amplitude modulated laser operating at a second wavelength; and
    a network analyzer adapted to receive said frequency division multiplexed electrical signals from the photodetector and to determine the change in the respective resonant frequency of each of the microbeams,
    wherein in operation, a frequency of amplitude modulation of the amplitude modulated laser is swept through a frequency range including the fundamental resonant frequencies of all the microbeams with and without sorbed analytes to photothermally actuate the microbeams into resonance.

5. The sensor system according to claim 1, wherein the plurality of microbeams includes four microbeams.

6. The sensor system according to claim 1, wherein the plurality of microbeams includes six microbeams.

7. The sensor system according to claim 1, wherein each of the microbeams has a different length.

8. The sensor system according to claim 1, wherein each of the microbeams is a microbridge having two ends, each of said two ends being connected to the substrate by a support post.

9. The sensor system according to claim 1, wherein each of the microbeams is a microcantilever, each of the microcantilevers having an end connected to the substrate by a support post.

10. The system according to claim 1, wherein the sorbent materials are polymers selectively applied to each microbeam using a microneedle.

11. The system according to claim 1, wherein each microbeam is different in width, intrinsic strain, or material composition, with a difference in the respective resonant frequency being at least a few percent between any two of the microbeams.

12. The system according to claim 1, wherein the amplitude modulated laser operates at a wavelength of 1310 nanometers, and the interrogation laser is tunable over a wavelength of 1440 nm to 1640 nm.

13. The system according to claim 1, wherein said analyte is a chemical and said sorbent materials are chemoselective polymers.

14. A method for detecting a target vapor-phase analyte, comprising:
    providing a sensor having a transparent substrate, a plurality of microbeams connected to the substrate, at least two of the microbeams having a different sorbent material disposed thereon, each of the microbeams including a reflective material and having a different fundamental resonant frequency;
    exciting the plurality of microbeams into resonance; and
    simultaneously interrogating all of the microbeams by illuminating all of the microbeams with a single laser spot from an interrogation laser operating at a first wavelength,
    reflected optical energy from the microbeams due to said interrogating producing frequency division multiplexed electrical signals indicating the respective resonant frequency of each of the microbeams, wherein a change in the respective resonant frequency of a respective microbeam from its fundamental resonant frequency without sorbed analytes indicates sorption of the target analyte by the sorbent material disposed on the respective microbeam.

15. The method according to claim 14, wherein said exciting comprises photothermal excitation by an amplitude modulated laser operating at a second, different, wavelength and comprises sweeping the frequency of amplitude modulation through a range of frequencies including the respective fundamental resonant frequencies of all the microbridges with and without sorbed analytes.

16. The method according to claim 15, wherein the sensor includes a reflective material disposed on the transparent substrate, and wherein each microbeam is connected at an end to the substrate by a support post, the method further comprising:

interferometrically determining a change in reflectivity of the microbeams, wherein a change in reflectivity of one of the microbeams indicates a change in the respective resonant frequency of said one of the microbeams due to adsorption of the target analyte by the sorbent material disposed on said one of the microbeams.

17. The method according to claim 15, further comprising:

combining energy from said amplitude modulated laser and said interrogation laser in a wave division multiplexer; and transmitting said combined energy to the sensor through a single optical fiber aperture such that the single laser spot illuminates all of the microbeams.

18. The method according to claim 15, wherein a single optical fiber aperture transmits energy from the amplitude modulated laser and the interrogation laser to all the microbeams and to the reflective material of all the microbeams and receives the reflected optical energy from the microbeams and from the reflective layer of the microbeams.

19. The method according to claim 14, wherein a portion of energy of the amplitude modulated laser is received at the substrate and transmitted through the substrate to all of the microbeams.

20. The method according to claim 14, wherein the frequency of amplitude modulation is close to the respective fundamental resonant frequencies of all the microbeams.

21. The method according to claim 14, wherein each of the microbeams has a different length within a range of between about 180 microns and about 220 microns.

22. The method according to claim 14, wherein a different sorbent material is disposed on each of the microbeams.

23. The method according to claim 14, wherein the sensor has at least one reference microbeam free of sorbent material.

24. The method according to claim 14, further comprising:

receiving said reflected optical energy at a photodetector;

transmitting signals from the photodetector to a network analyzer; and determining at said network analyzer the change in the respective resonant frequencies of each of the microbeams.

25. The method according to claim 24, further comprising:

distinguishing the presence of a particular target chemical class based on said change in the respective resonant frequencies.

26. The system according to claim 14, wherein said analyte is a chemical and said sorbent materials are chemoselective polymers.

* * * * *